(12) United States Patent
Brandestini

(10) Patent No.: US 8,261,620 B2
(45) Date of Patent: Sep. 11, 2012

(54) METHOD AND APPARATUS FOR THE NON-DESTRUCTIVE MEASUREMENT OF THE COMPRESSIVE STRENGTH OF A SOLID

(75) Inventor: Marco Brandestini, Schwerzenbach (CH)

(73) Assignee: Marco Brandestini, Schwerzenbach (CH)

( * ) Notice: Subject to any disclaimer, the term of this patent is extended or adjusted under 35 U.S.C. 154(b) by 212 days.

(21) Appl. No.: 12/679,117

(22) PCT Filed: Sep. 20, 2007

(86) PCT No.: PCT/CH2007/000464
§ 371 (c)(1),
(2), (4) Date: Apr. 21, 2010

(87) PCT Pub. No.: WO2009/036578
PCT Pub. Date: Mar. 26, 2009

(65) Prior Publication Data
US 2010/0307258 A1     Dec. 9, 2010

(51) Int. Cl.
*G01N 3/00*     (2006.01)
(52) U.S. Cl. ......................................... 73/803
(58) Field of Classification Search ............... 73/12.01, 73/12, 9, 79, 803, 12.09
See application file for complete search history.

(56) References Cited

U.S. PATENT DOCUMENTS

| 4,034,603 A | | 7/1977 | Leeb et al. | |
| 4,886,255 A | * | 12/1989 | Paton | 267/205 |
| 5,176,026 A | * | 1/1993 | Leeb et al. | 73/79 |
| 5,311,764 A | | 5/1994 | Smith et al. | |
| 5,672,809 A | * | 9/1997 | Brandt | 73/12.01 |
| 5,827,953 A | * | 10/1998 | Sato et al. | 73/79 |
| 5,959,198 A | | 9/1999 | Pollok et al. | |
| 6,354,148 B2 | * | 3/2002 | Sato et al. | 73/79 |
| 6,976,387 B2 | * | 12/2005 | Anthe et al. | 73/83 |
| 7,284,414 B2 | * | 10/2007 | Wu | 73/79 |
| 2001/0010170 A1 | | 8/2001 | Sato et al. | |
| 2006/0130566 A1 | | 6/2006 | Wu | |

FOREIGN PATENT DOCUMENTS

| DE | 19514857 A1 | 10/1996 |
| DE | 202 14 568 | 4/2003 |
| EP | 1 251 343 | 10/2002 |

(Continued)

OTHER PUBLICATIONS

A. Basu, A. Aydin; International Journal of Rock Mechanics & Mining Sciences 41 (2004) 1211-1214; Entitled: A method for normalization of Schmidt hammer rebound values. Date Accepted: May 6, 2004; Date Available Online: Jun. 19, 2004.

(Continued)

*Primary Examiner* — Max Noori
(74) *Attorney, Agent, or Firm* — Marshall, Gerstein & Borun LLP

(57) ABSTRACT

An apparatus and a method are described that determine the compressive strength of a solid by rebound. The method and apparatus have a reduced sensitivity to error sources, i.e. gravity, internal friction and operator interference (unsteady holding of the instrument). The improvements are achieved by contactless measuring of the quotient of rebound to inbound velocity recorded immediately before and after the impact. Matching the mass of the mallet (3) to the plunger (5) yields higher efficiency, less angular variation of the impact energy and lighter weight. Added benefits of the invention are: Extended range of measurement and simplified mechanical adjustments, calibration and maintenance.

16 Claims, 4 Drawing Sheets

| | FOREIGN PATENT DOCUMENTS | |
|---|---|---|
| GB | 989944 | 4/1965 |
| JP | 10-227732 A | 8/1998 |
| JP | 10227732 | 8/1998 |
| JP | 2002-267583 A | 9/2002 |
| JP | 2002267583 | 9/2002 |
| JP | 2005-114490 A | 4/2005 |
| JP | 2005-147995 A | 6/2005 |
| JP | 2005-265766 A | 9/2005 |
| WO | WO-96/34267 A1 | 10/1996 |
| WO | WO-2006/136038 A1 | 12/2006 |

OTHER PUBLICATIONS

International Search Report and Written Opinion based on PCT/CH02007/000464; Date of Mailing May 7, 2008.
European Search Report for European Application No. 07 800 655.8-1234, dated Sep. 17, 2010.
Translation of the Notification of Reasons for Refusal for Japanese Application No. 2010-525176 dated May 2, 2012.

* cited by examiner

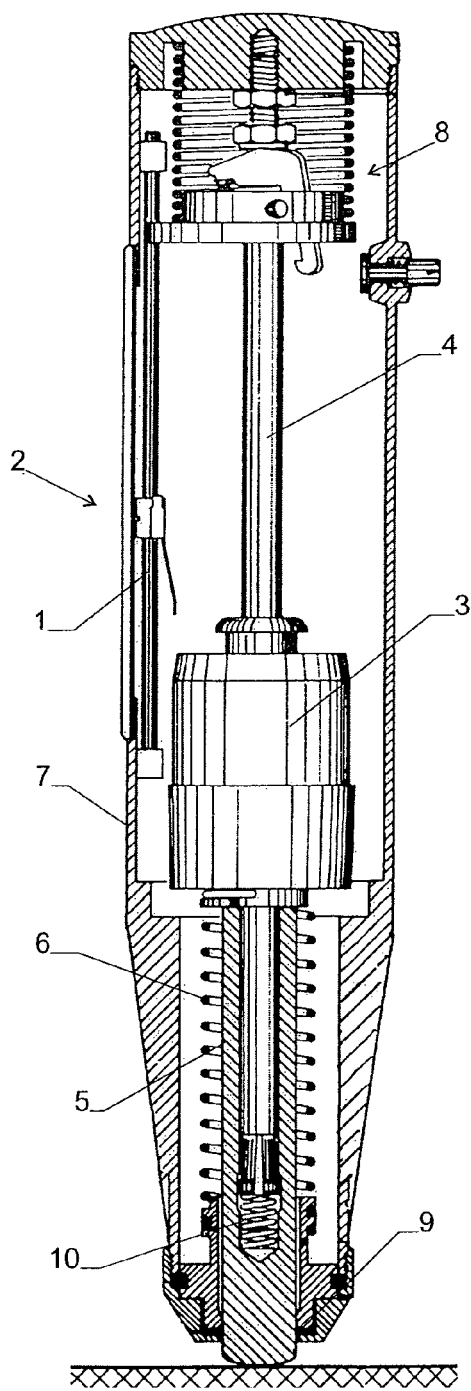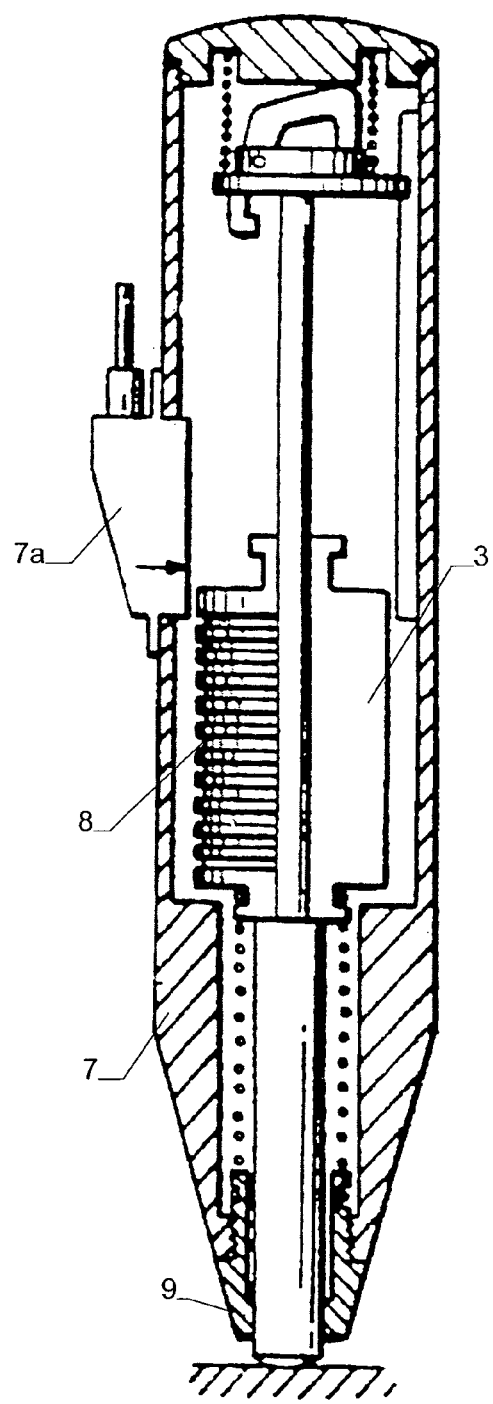
*Fig .1*  *Fig. 2*

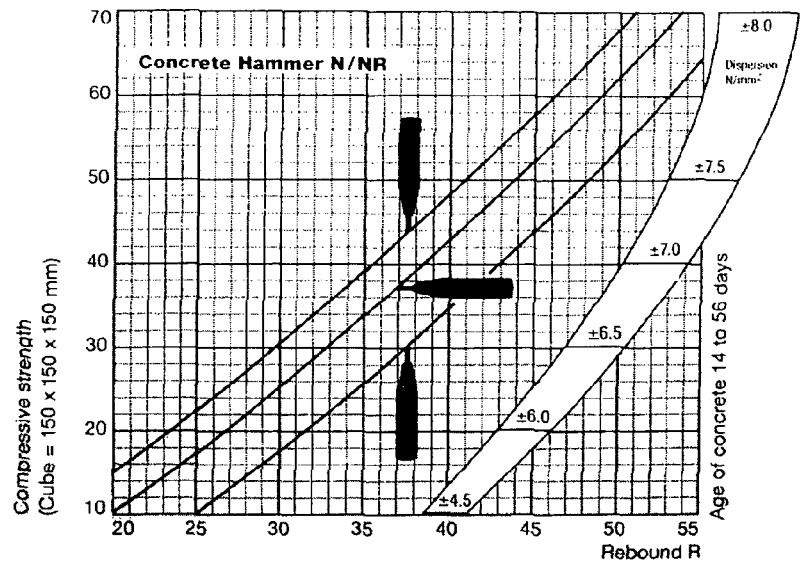
Fig. 3
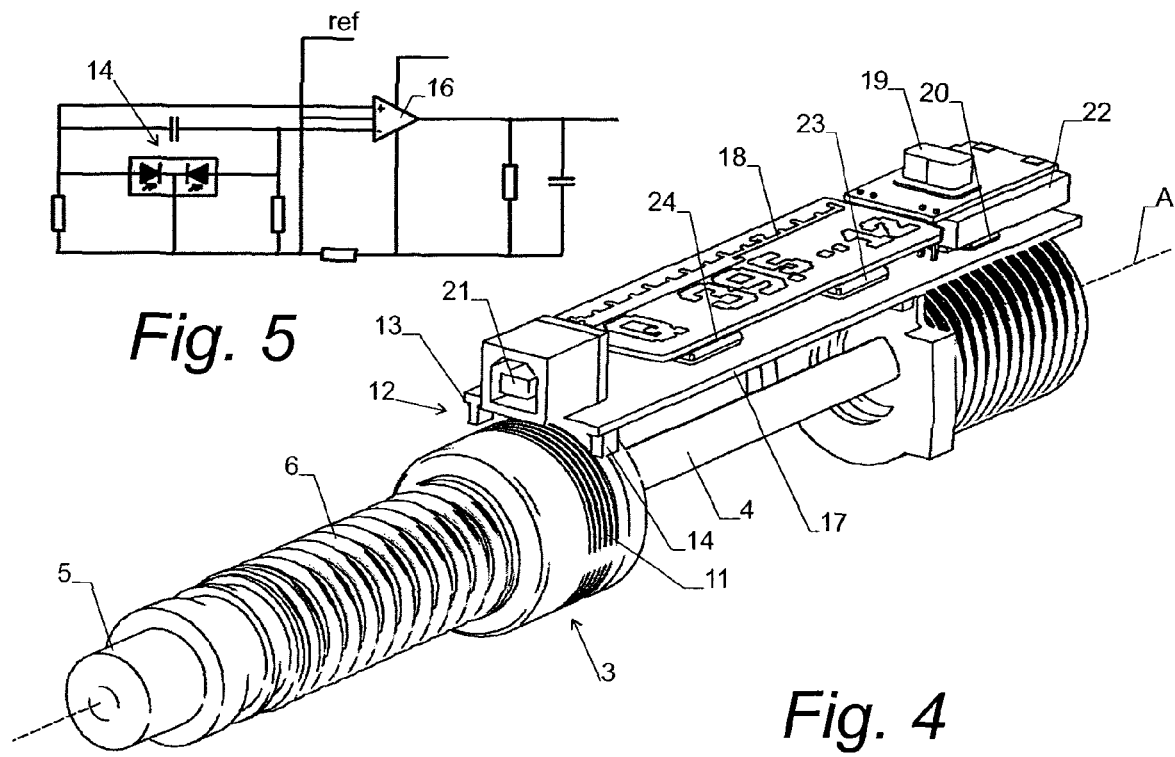
Fig. 5
Fig. 4

US 8,261,620 B2

METHOD AND APPARATUS FOR THE NON-DESTRUCTIVE MEASUREMENT OF THE COMPRESSIVE STRENGTH OF A SOLID

TECHNICAL FIELD

The invention relates to a method and apparatus for the non-destructive measurement of the compressive strength of a solid, in particular of concrete.

BACKGROUND ART

Since the fifties methods have been in use to assess the compressive strength of concrete using an apparatus with a defined tip to impact upon the surface to be tested.

The best known method is the so-called Schmidt hammer that generates a defined impact energy by extending a spring and letting it drive a mallet. This mallet in turn hits upon a plunger that transfers the impact to the surface to be tested.

Upon impact the concrete is compressed and part of the energy is absorbed by plastic deformation. The remaining energy is returned and causes the plunger to rebound. The rebound is then transferred back to the mallet. The mallet then compresses the spring until the kinetic energy of the mallet is fully transferred into deformation energy of the spring. The point of this maximum compression of the spring is registered by means of a drag pointer. Its position is readable from the outside of the instrument. The reading of this instrument is expressed as R-value, meaning the maximum rebound travel of the mallet. Typically R-values range from R=20 to R=55.

FIG. 3 shows how the rebound values of the mallet can be converted to an indication of compressive strength. Note that there is a substantial influence of the angle at which the unit operates, as indicated by the three curves. When measuring inclined surfaces the angle has to be estimated and the values must be interpolated from the curve set.

In the present art the signal of interest is falsified by several error factors. Typically these can total up to 15, even 20% of the measured value. The smaller the rebound energy, the greater the percentual error contribution. Especially for rebound values less than 20 the energy absorbed by gravity and friction can be close to the rebound energy (article Dr. K. Gaede, volume 154 Schriften des Deutschen Ausschusses für Stahl-beton).

To keep the influence of friction to a minimum, the apparatus must be carefully adjusted, cleaned and inspected frequently—all factors increasing the cost of the device and leading to a limited acceptance of the rebound method.

With the advent of digital electronics and LCD displays many companies have "digitized" their instruments. Instead of having to read the position of the mechanical drag pointer, these units feature a numeric display. Up to this point such instruments have simply converted the final position of the drag pointer into an electrical value either by contacting means or non contacting (optical, Hall sensors etc.). The indicator electronics can either be a separate box or mounted right on the instrument. Such units have been in the market for over a decade.

FIG. 1 is a sectional view of a typical Schmidt hammer equipped with a linear potentiometer 1 to convert the position of the drag pointer 2 to an electrical value, which is transmitted to an external indicator unit via a connector. All the other mechanical parts are 100% identical to the original, mechanical Schmidt hammer. We note the mallet 3 that travels on the guide rod 4 and hits the plunger 5 drawn by the impact spring 6. Housing 7 and release/reload mechanism 8 are mentioned for the sake of completeness.

"Integrated" models with numeric readouts are based on standard mechanical units equipped with sensing circuitry for the drag pointer.

All these solutions suffer from the problems inherent to mechanical drag pointer indicators:

1) The rebound value is dependent on the inclination of the surface under test (effect of gravity on the mallet).

2) The readings remain dependent on the internal friction of the apparatus (mallet traveling on guide rod plus friction of drag pointer).

3) The transfer efficiency of the kinetic energy between the mallet and the plunger is not constant due to the mismatch of the two masses.

4) The impact energy (length of spring) and the zero position of each instrument have to be manually adjusted, which increases cost and the chance of maladjustments.

5) The impact energy is dependent on the angle of incidence due to gravity.

6) The readings remain dependent on the way the operator actuates the apparatus—vigorously or hesitantly (velocity of housing with respect to fixed coordinate system).

U.S. Pat. No. 5,176,026 (Leeb, Brunnner) (FIG. 2) describes an apparatus which measures the rebound travel of the mallet by means of a transducer consisting in a reflective optical detector 7a and a mallet 3 featuring grooves 8 filled with an opaque substance on its entire length. This approach eliminates the drag pointer and its friction, whereas the other error sources (effect of gravity on mallet, friction of mallet on guide rod, zero position of spring) are still affecting the result. Furthermore the reflective sensor scheme is lacking due to its susceptibility to dirt and fingerprints. This type of device has been of limited commercial success. The implementation shown in FIG. 1, although "cruder" in its design, remains the state-of-the-art.

Attempts have been made to apply a technique that is used in assessing the hardness of metals (U.S. Pat. No. 4,034,603) to the Schmidt hammer—so far these efforts have failed.

In this technique—intended for shop use—the mallet directly impinges on the sample and the housing of the impact device rests on the surface under test.

Note:

a) The Schmidt hammer is used mainly under outdoor conditions and must be sealed against dust and moisture, therefore the mallet cannot impinge directly on the surface under test, but must transfer its energy via the plunger 5. This design allows for a seal 9 between the moveable plunger 5 and the instrument housing 7.

b) The loading and trigger mechanism of the Schmidt hammer is such that the unit rests on the plunger and not on the housing of the instrument.

DISCLOSURE OF THE INVENTION

Hence, it is a general object of the invention to provide an apparatus of the type above that measures a more accurate parameter indicative of the compressive strength of the solid under test.

This object is achieved by the apparatus and method of the independent claims.

Accordingly, the apparatus is equipped with a sensor that measures at least two rebound velocities of the mallet at different times during its rebound motion. Using the at least two measured velocities, the control unit of the apparatus then calculates a parameter that is indicative of the compressive strength of the solid.

This technique is based on the understanding that a measurement of the velocity immediately after impact is more accurate than the conventional measurement of the rebound height because the rebound velocity can be measured at an earlier stage of the rebound motion and therefore is much less prone to errors due to gravity and friction. In addition, it is based on the understanding that a single measurement of the rebound velocity will suffer from errors due to the strong mechanical disturbances the instrument is subjected to during rebound. These disturbances are primarily due to the repercussions of the impacts between mallet and plunger and between plunger and solid. However, since the mechanical disturbances only cause temporary glitches in the measurement, the detection of two or more velocities allows to recognize and/or eliminate their influence efficiently.

Advantageously, the apparatus is further adapted to measure at least one, in particular at least two, inbound velocities of the mallet prior its impact against the plunger. The inbound velocity or velocities can be used to further refine the measured parameter because knowledge of the inbound velocity allows to account for errors prior to the impact, such as gravity, friction and spring fatigue.

Advantageously, the apparatus is further adapted to compute the quotient of rebound versus inbound velocity, each taken at the same relative location between mallet and housing.

Advantageously, the plunger has a mass that is substantially equal to the mass of the mallet. The advantages of this measure are two-fold. On the one hand, an equality of these masses ensures a full energy transfer between mallet and plunger and therefore increases the accuracy of the instrument. In particular, the impact brings the mallet substantially to a stop, while its full kinetic energy is transferred to the plunger. While the mallet is substantially stationary, the plunger hits the solid and bounces back to transfer all its remaining energy back to the plunger. In contrast to this, in prior art instruments the mallet is generally much heavier than the plunger. Therefore, the energy transferred to the plunger is smaller, and the mallet does not come to a stop after impact and tends to hit the plunger several times, thereby making the measurement unpredictable. In addition, only part of the energy of the plunger is transferred back to the mallet, thereby decreasing the sensitivity of the device. Finally, using a mallet that is lighter than prior art instruments allows to accelerate it to a higher speed, thereby decreasing the time span for gravity to affect its motion and further increasing the accuracy of the instrument. The reduced variation of impact velocity/energy helps to ensure the impact energy stays within the tolerance specified by national standards. Also, the instrument has smaller overall mass.

The invention is particularly suited for the measurement of the compressive strength concrete.

The invention relates to an apparatus as well as a method. In particular, it is noted that any method-related features of the claims relating to the apparatus can also be formulated as claims relating to the method, and vice versa.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 shows a first prior art instrument equipped with a linear potentiometer,

FIG. 2 is a second prior art instrument equipped with a mallet having a reflective pattern on its entire length, FIG. 3 is a graph showing the conversion curves for a prior art Schmidt hammer, FIG. 4 is a perspective view of key components of a preferred embodiment of the apparatus, FIG. 5 shows the circuitry for processing the signals from the optical detectors.

MODES FOR CARRYING OUT THE INVENTION

Figure 6:
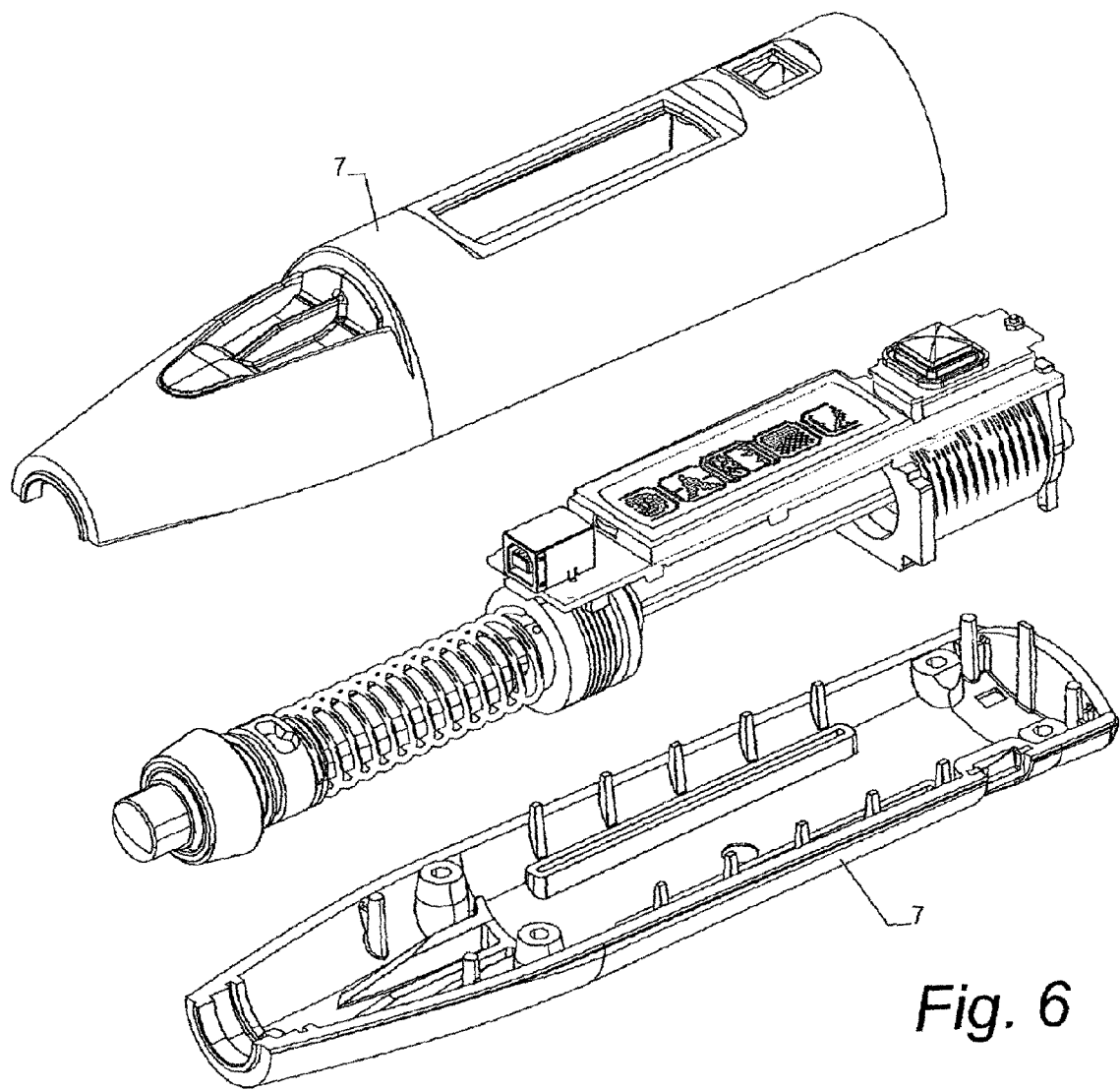
FIG. 6 is an exploded view of the device.

FIG. 4 shows the relevant parts of an advantageous embodiment of the device at the time of impact. The housing has been omitted for simplicity (FIG. 6 shows the complete hammer unit). We note the mallet 3, which travels along an axis A on a guide rod 4 and impinges on the plunger 5 drawn by the impact spring 6, with impact spring 6 acting as a drive mechanism for driving mallet 3 against plunger 5. These parts are virtually identical to the classic implementation as e.g. described in U.S. Pat. No. 5,176,026. However, the mass of the mallet 3 is now reduced to match the mass of the plunger. This is to ensure that the energy of the mallet is transferred to the plunger in one single blow, when it travels toward the plunger and from the plunger to the mallet upon return. In the classic unit there are multiple contacts of a random number, whereby a part of the energy is lost. Further advantages of this design have been described above.

Note that the impact spring 6 is the same as in prior art instruments; it features a spring constant of 0.79 N/mm and is extended to 75 mm yielding an impact energy of: E=2.22 Nm.

The mallet 3 weighs only 115 grams, therefore it travels with a higher velocity. V=sqrt (2*E/m)=6.21 m/s. The time of travel is therefore reduced and likewise the effect that gravity has on accelerating or decelerating the mallet.

To measure the velocity of the mallet 3, it is equipped with a number of circumferential ribs 11 of trapezoidal cut that form projections on its cylindrical outer surface. These ribs are located such that upon passage they interrupt the beam of a dual light barrier 12. The beam is oriented tangentially with respect to the mallet 3.

The dual light barrier 12 comprises an infrared light source 13 and a dual light detector 14 having two sensor areas of 1 $mm^2$ and arranged such that each of them will alternately be illuminated or shadowed upon passage of the mallet 3 and its ribs 11 at the location of light barrier 12.

As shown in FIG. 5, the output of the two sensor areas are connected to a differential amplifier 16 (TI INA321). Its output is connected to the A/D port of a control unit 24 (TI MSP430G) arranged on a printed circuit board 17 within the device.

Note how the stationary part of the encoder, namely light barrier 12, is also directly located on the circuit board 17. Circuit board 17 further carries all other electronic components, in particular a dot matrix display 18 with its controller 23, a battery 22 and a single button 19 to control the unit.

A two axis accelerometer 20 is also arranged on circuit board 17. It serves multiple tasks. It monitors the acceleration of the housing during the measurement phase and allows for compensation of its movement. It also detects the angle of inclination and can make fine adjustments to the measured parameters.

It is further used in lieu of a cursor key to scroll (move), swap or orient the text and symbols displayed on display 18. In particular, it can detect which side of the device is up and which is down, and, based on this, rotate the text in the display for best readability. It also can cause a long text or image displayed on the text to be scrolled or moved along the display when the user tilts the display in a defined direction.

A USB connector 21 is provided to charge the battery and to interface the unit to an external device, e.g. a PC.

FIG. 6 shows how the present design allows to encapsulate the entire unit in a housing 7 that completely seals it against dust and moisture.

Figure 7:
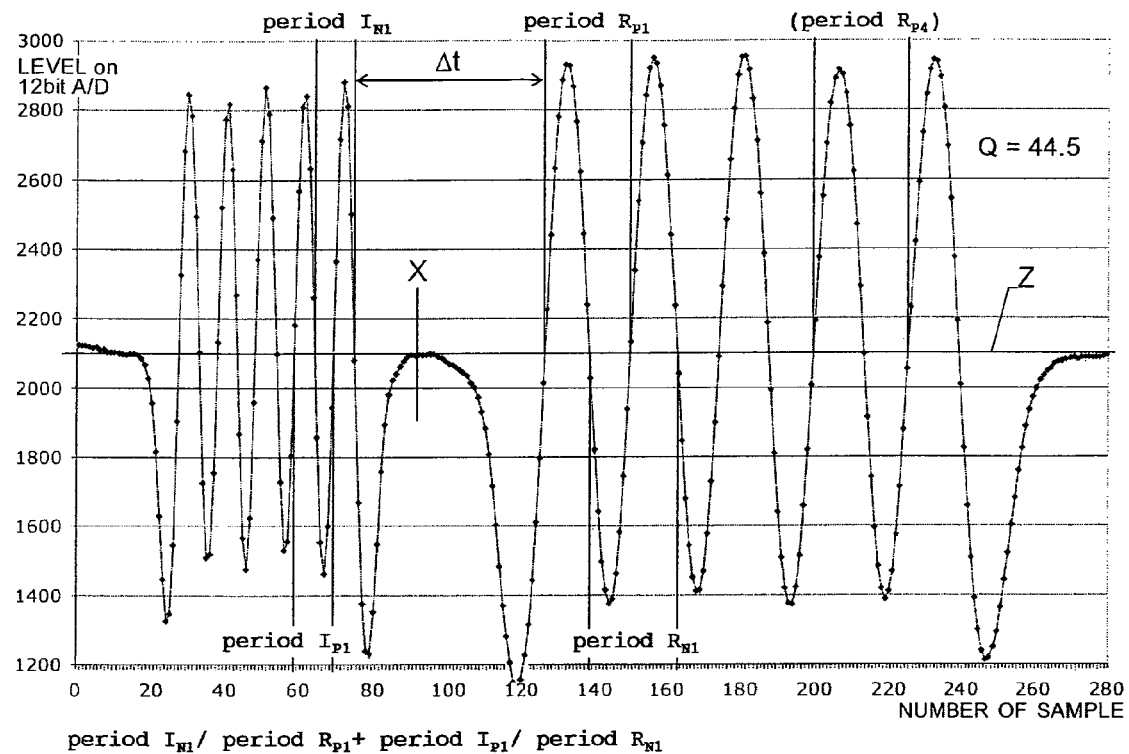
FIG. 7 is a sample waveform as detected by the sensor.

FIG. 7 shows a typical signal such a sampled by the 12 bit A/D converter of control unit 24, where the approximate instant of impact between mallet and plunger is denoted by a line X.

As can be seen, a series of signal oscillations is detected prior to impact and during rebound of the mallet. The frequency or period of these oscillations is indicative of the velocity of the mallet.

In the present embodiment, the absolute velocity is detected at least twice prior to impact and at least twice during rebound. The velocities are measured by computing the zero crossings of the signal and by calculating the distances between consecutive rising or falling zero crossings.

In the example of FIG. 7, at least a first and a second average inbound velocity at different times are calculated prior to impact from the period $I_{N1}$ between the last two falling zero crossings and from the period $I_{P1}$ between the last two rising zero crossings. Similarly, a first and a second average rebound velocity at different times are calculated during rebound from the period $R_{P1}$ between the first two rising zero crossings and from the period $R_{N1}$ between the first two falling zero crossings.

The sample rate of the signal from amplifier 16, indicated by the dots in FIG. 7, is comparatively low with respect to the waveform to be analyzed. In order to attain enough resolution, the precise occurrence of the zero crossings is obtained by a linear interpolation between the two samples on either side of the zero line Z.

In essence the waveform detected by the photo interrupter is symmetrical. The right side is stretched by the factor of inbound/rebound velocity.

Careful observation shows, however, a decrease of velocity as one moves further away from the point of impact X as a result of friction, gravity and spring back-force.

Therefore, advantageously, we determine the quotient of rebound to inbound velocity, the "Q" factor, by pair wise division of the corresponding periods in close proximity of the point impact. The pair wise division is best carried out by dividing the rebound and impact velocities that were measured on the same section of the mallet. Namely, the first rebound velocity $v_{r1}$ derived from period $R_{P1}$ is divided by the first inbound velocity $v_{i1}$ derived from period $I_{N1}$ to calculate a first Q-factor $Q_1=100*(I_{N1}/R_{P1})$ because both $v_{r1}$ and $v_{i1}$ were measured on the same rib 11 of mallet 3. Therefore, errors due to dirt or mechanical imperfections of the rib will be eliminated. Similarly, the second rebound velocity $v_{r2}$ derived from period $R_{N1}$ is divided by the second inbound velocity $v_{i2}$ derived from period $I_{P1}$ to calculate a second Q-factor $Q_2=100*(I_{P1}/R_{N1})$. The final Q-factor, which will be used to compute the compressive strength of the solid, is calculated as the average $Q=(Q_1+Q_2)/2$.

More quotients could be averaged or processed using statistics, but one has to consider that, due to friction, gravity and the spring force, the velocity will change as the samples are taken further away from the time of impact.

On the other hand the decrease of rebound velocity can be assessed and used to alert the user to the presence of excessive friction in the system.

The "Q" factor can be considered as the "true" rebound coefficient, since it is virtually unaffected by the aforementioned side effects. The inventive method therefore does not set a new standard for assessing concrete compressive strength, but will yield more reliable results over an extended range.

The inbound velocity can further be used to verify the impact energy specified by international standards to be 2.207 Nm±6%.

Typically: $E=0.5*0.115 \text{ kg}*(6.21 \text{ m/s})^2=2.22$ Nm

Since the mass of the mallet is constant, monitoring the impact energy substantially corresponds to comparing the inbound velocity to an allowable range of inbound velocities (or equivalently, comparing one of the periods of the inbound signal trace of FIG. 7, such as $I_{N1}$ or $I_{P1}$, to an allowable time range). The device can issue an alert if the inbound velocity does not fall within the allowable range. By reading the accelerometer output the device can differentiate which part of the inbound velocity is caused by gravity and which by the drive mechanism.

(At this point the reader can see an important difference between the prior art U.S. Pat. No. 5,176,026 (Leeb, Brunner) where a reflective optical scheme is used, however to assess the rebound travel of the mallet and not its velocity, let alone the quotient of rebound to inbound velocity).

The Q-factor is a parameter indicative of the compressive strength of the solid. It can be converted to physical units, like $N/mm^2$, by carrying out a large number of laboratory and field tests, where cubes measuring 150×150×150 mm are assessed with the inventive device and subsequently crushed by means of a press.

Figure 8:
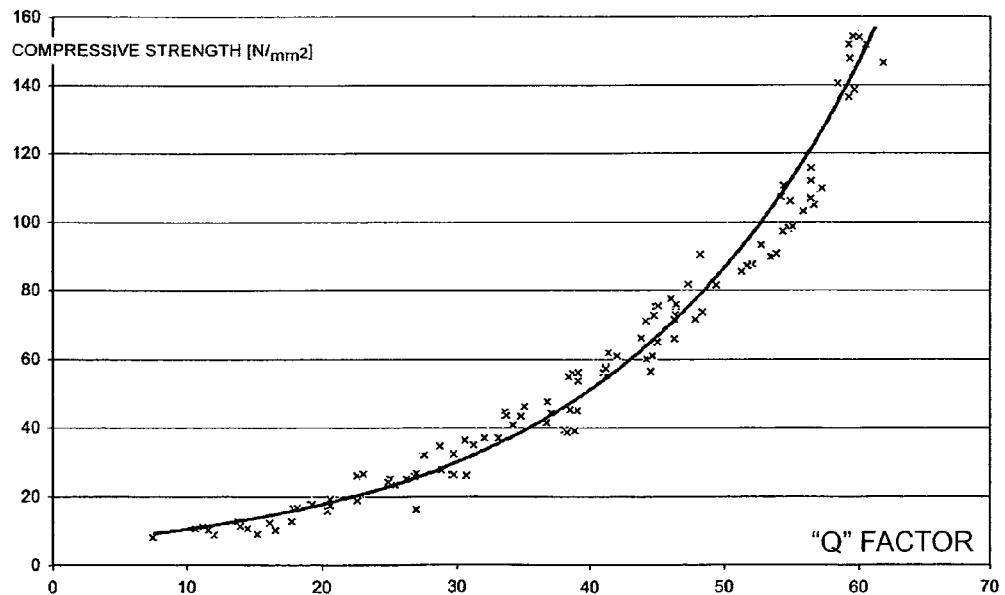
FIG. 8 is a graph showing conversion of "Q" factor to compressive strength.

A graph showing the relationship between compressive strength and the "Q" factor is given in FIG. 8. Note that there is but one conversion curve for all possible angular orientations of the surface under test. For the reasons outlined above the curve is not unlike the one applicable to the mechanical Schmidt hammer. (As a coarse approximation one may set: $Q \approx R \times 1.12$). The "Q" scale accommodates a wide range of compressive strengths, from 5 to 150 N/mm2 and beyond.

Calibration data describing the curve of FIG. 8 can be stored in the control unit of the present device, thereby allowing it to convert the measured "Q" factor to the compressive strength of a cube. The conversion to compressive strength is done after having computed an average of a sufficient number of "Q" factors.

The result of the measurement can be displayed in the form of a bar and/or as a number on display 18. The result can e.g. be the "Q" factor, the compressive strength of a cube as obtained by the curve of FIG. 8, or any other suitable value descriptive of the strength of the measured material.

As can be seen from FIG. 4 and as it also follows from the signals in FIG. 7, the projections or ribs 11 are arranged such that they are located in the range of the light barrier 12 at the time of impact, which allows to measure the inbound and rebound velocities immediately prior to impact and right at the beginning of the rebound motion. Hence, the measured velocities represent the situation during impact in an optimum manner and are not falsified by friction, gravity or the braking action of spring 6 on mallet 3.

As mentioned, an accelerometer 20 is provided in the present device. Its output signals are used by the control unit to correct the measured parameter.

Advantageously, accelerometer 20 should at least be able to measure the acceleration along axis A, which allows to assess the influence of gravity and sudden motions of the device's housing on the movement of the mallet and to correct the measured results.

In particular, if accelerometer 20 measures a constant, non-zero acceleration along axis A during the measurements of the mallet motion (i.e. during the time span between release of the mallet and period $I_{P1}$ and $R_{N1}$ in the example above), it is assumed that the housing has not been accelerated during the measurements but that a constant gravity component was influencing the motion of mallet 3. In that case, the inbound velocities $v_{i1}$ and $v_{i2}$ as well as the rebound velocities $v_{r1}$ and $v_{r2}$ need not be corrected.

If a non-constant, significant acceleration is measured along axis A, the same can be split up into a constant contribution representing gravity and a non-constant contribution representing an acceleration a of the housing. The constant acceleration is attributed to gravity, while the non-constant acceleration component can be integrated to calculate the velocity of the housing at the times of the measurements of the inbound and rebound velocities and added/subtracted from the same accordingly:

$$v'_{rk} = v_{rk} + \int_0^{t_{rk}} a \, dt \text{ and}$$

$$v'_{ik} = v_{ik} - \int_0^{t_{ik}} a \, dt$$

with k=1 ... N and N being the number of velocity measurements prior and after impact (N=2 for the example above), v' denoting the corrected velocity measurements, $t_{rk}$ the time span between the measurement of $v_{rk}$ and the release of the mallet, $t_{ik}$ the time span between the measurement of $v_{ik}$ and release of the mallet, and a being the measured acceleration along axis A.

The time of impact as well as the energy of the mallet during impact depends on where the plunger is located at that time. In particular, it must be noted that a small spring (denoted by reference number 10 in the prior art embodiment of FIG. 1) is arranged between guide rod 4 and plunger 5 to uncouple the plunger 5 from the guide rod 4 during impact. Depending on how strongly the user presses the instrument against the solid under test, the length of that spring varies and therefore (since guide rod 4 is fixedly connected to housing 7) the impact position of plunger 5 may vary. For example, if the user presses the device strongly against the solid, the plunger will rest more deeply within the instrument and the path length for accelerating mallet 3 will be shorter as compared to a situation where the user presses the device weakly against the solid.

The position of the plunger during impact can be derived from the position of the first and last oscillations of the signal of FIG. 7 before and after impact X. In the example of FIG. 7, the time interval Δt between the last falling zero crossing before impact X and the first rising zero crossing after impact depends on the position of plunger 5 during impact. This time interval Δt corresponds to the time span between the time when the last edge of a rib 11 passes the sensor 13 prior to impact and the time when the same edge passes the sensor 13 during rebound. Instead of a rib edge, any other detectable mark on the mallet could be used for this measurement.

In an advantageous embodiment, reference measurements are carried out with the instrument against a sample of known compressive strength for different plunger positions. For each measurement, the time interval Δt and the deviation of the measured parameter from a correct value of the parameter is recorded. This allows to establish heuristic calibration data describing how to correct the value of the measured parameter as a function of time period Δt. This calibration data is stored in control unit 24.

The described device has a large number of advantages. It particular, it accurately records a parameter indicative of compressive strength without the need for correction of the angular inclination of the apparatus. It accurately measures the velocity of the mallet immediately before and after the impact in a non-contacting way, thereby yielding results that are substantially unaffected by gravity and friction as well as by the braking action of spring 6 during rebound. It yields reliable results for a range of compressive strengths both above and below the currently attainable values, e.g. 5 to 150 $N/mm^2$. It provides a display featuring a user-friendly readout right on the unit. Further, the device is easy to assemble, to calibrate and to service.

While there are shown and described presently preferred embodiments of the invention, it is to be distinctly understood that the invention is not limited thereto but may be otherwise variously embodied and practiced within the scope of the following claims.

The invention claimed is:

1. An apparatus for the non-destructive measurement of the compressive strength of a solid, in particular of concrete, comprising
    a plunger displaceable along an axis and having a front end for probing the solid,
    a mallet displaceable along said axis to impact against said plunger,
    a drive mechanism for driving said mallet against said plunger, thereby causing said plunger to impact against said solid and to generate a rebound of said mallet,
    a sensor measuring at least two rebound velocities of said mallet at different times during said rebound, and
    a control unit calculating a parameter indicative of the compressive strength of said solid depending said at least two rebound velocities
    comprising a plurality of projections on a surface of said mallet and wherein said sensor comprises a light barrier generating at least one light beam interrupted by said projections.

2. The apparatus of claim 1 wherein said sensor is further adapted to measure at least one inbound velocity of said mallet prior to impact against said plunger, and wherein said control unit is adapted to calculate said parameter depending on said at least one inbound velocity.

3. The apparatus of claim 2 wherein said control unit is further adapted to compare said inbound velocity to an allowable range of inbound velocities and to generate an alert if said inbound velocity does not fall within said allowable range of inbound velocities.

4. The apparatus of claim 3 wherein said control unit is adapted to generate a quotient (Q) between said inbound velocity and at least one of said rebound velocities.

5. The apparatus of claim 1 wherein said sensor is further adapted to measure at least two inbound velocities of said mallet at different times prior to impact, and wherein said control unit is adapted to calculate said parameter depending on said at least two inbound velocities.

6. The apparatus of claim 5 wherein said sensor is adapted to measure at least a first inbound velocity and a first rebound velocity when a first section of said plunger passes said sensor and a second inbound velocity and a second rebound velocity when a second section of said plunger passes said sensor, and wherein said control unit is adapted to calculate at least a first ratio ($Q_1$) of said first rebound and impact velocities and a second ratio (Q2) of said second rebound and impact velocities.

7. The apparatus of claim 6 wherein said control unit is adapted to calculate an average of said ratios (Q1, Q2).

8. The apparatus of claim 1 wherein said plunger has a mass substantially equal to the mass of said mallet.

9. The apparatus of claim 1 further comprising at least one accelerometer, wherein said control unit is adapted to correct said parameter depending on a signal generated by said accelerometer.

10. The apparatus of claim 9 wherein said accelerometer is adapted to measure an acceleration along said axis.

11. The apparatus of claim 9 further comprising a display for displaying at least said parameter, wherein said apparatus is adapted to orient and/or move a displayed text depending on an orientation of said apparatus as measured by said accelerometer.

12. The apparatus of claim 1 wherein said control unit is adapted to measure an impact position of said mallet against said plunger and to use said impact position when calculating said parameter.

13. The apparatus of claim 12 wherein said sensor is adapted to detect a passage of a first mark on said plunger, wherein said control unit is adapted to measure said impact position from a time interval ($\Delta T$) passing between the passage of the first mark prior to impact and during rebound.

14. The apparatus of claim 1 wherein said projections are located to be positioned in a range of said light barrier at a time of said impact.

15. The apparatus of claim 1 wherein said sensor comprises at least two light detectors subsequently shadowed by said projections during a passage of said mallet and an amplifier circuit measuring a difference of signals from said two light detectors.

16. The apparatus of claim 1 wherein said projections extend around a cylindrical outer surface of said mallet.

* * * * *

UNITED STATES PATENT AND TRADEMARK OFFICE
CERTIFICATE OF CORRECTION

PATENT NO. : 8,261,620 B2  Page 1 of 1
APPLICATION NO. : 12/679117
DATED : September 11, 2012
INVENTOR(S) : Brandestini It is certified that error appears in the above-identified patent and that said Letters Patent is hereby corrected as shown below:

In the Claims

Column 8, Line 27, Claim 1, delete "comprising" and insert -- comprising: --, therefor.

Column 9, Line 2, Claim 6, delete "(Q2)" and insert -- ($Q_2$) --, therefor.

Column 9, Line 5, Claim 7, delete "(Q1,Q2)." and insert -- ($Q_1,Q_2$). --, therefor.

Signed and Sealed this
Eighteenth Day of November, 2014

Michelle K. Lee
*Deputy Director of the United States Patent and Trademark Office*